(12) United States Patent
Mielnik et al.

(10) Patent No.: US 7,578,969 B2
(45) Date of Patent: *Aug. 25, 2009

(54) DECONTAMINATION SYSTEM FOR MAIL AND OTHER ARTICLES

(75) Inventors: Thaddeus J. Mielnik, Concord, OH (US); Matthew C. Mitchell, Willoughby, OH (US)

(73) Assignee: American Sterilizer Company, Mentor, OH (US)

( * ) Notice: Subject to any disclaimer, the term of this patent is extended or adjusted under 35 U.S.C. 154(b) by 1086 days.

This patent is subject to a terminal disclaimer.

(21) Appl. No.: 10/634,684

(22) Filed: Aug. 5, 2003

(65) Prior Publication Data

US 2009/0047173 A1 Feb. 19, 2009

Related U.S. Application Data

(63) Continuation-in-part of application No. 10/280,950, filed on Oct. 25, 2002, now Pat. No. 7,265,253.

(60) Provisional application No. 60/401,715, filed on Aug. 7, 2002, provisional application No. 60/416,917, filed on Oct. 8, 2002, provisional application No. 60/427,191, filed on Nov. 18, 2002.

(51) Int. Cl.
*A61L 2/00* (2006.01)

(52) U.S. Cl. .................................................. 422/28

(58) Field of Classification Search .................. 422/32, 422/28
See application file for complete search history.

(56) References Cited

U.S. PATENT DOCUMENTS 2,075,845 A 4/1937 Gross et al. .................. 167/39
4,111,753 A * 9/1978 Folsom et al. ................. 435/3
4,169,123 A 9/1979 Moore et al.
4,241,010 A * 12/1980 Baran ............................ 422/2
4,317,521 A * 3/1982 Clark et al. ................ 209/558

(Continued)

FOREIGN PATENT DOCUMENTS

DE 19537630 A1 * 4/1997

(Continued)

OTHER PUBLICATIONS

Wen, Sheree H.; Sterilizing Device and Method for Sanitizing Articles; Nov. 7, 2001.*

(Continued)

*Primary Examiner*—Jill Warden
*Assistant Examiner*—Kevin C Joyner
(74) *Attorney, Agent, or Firm*—Fay Sharpe LLP (57) ABSTRACT

A system for handling items (10) such as mail includes an enclosure (25), which is capable of being isolated from the surrounding environment and from a chamber (27) of a decontamination system (22) fluidly connected therewith. The enclosure includes an opening (42) sized for receiving a container (14) containing potentially contaminated items, such as incoming mail. Manipulators (44) allow the mail to be sorted in the enclosure without risk of contaminating an operator or the surrounding environment. Mail to be decontaminated is conveyed between the enclosure and the chamber while being isolated from the surrounding environment. Vapor hydrogen peroxide or other decontaminant gas is used to decontaminate the enclosure, container, and any residual mail in the enclosure which is determined to be unsuited for ethylene oxide processing.

26 Claims, 4 Drawing Sheets

U.S. PATENT DOCUMENTS

| | | |
|---|---|---|
| 4,909,999 A | 3/1990 | Cummings et al. |
| 5,068,087 A | 11/1991 | Childers |
| 5,173,258 A | 12/1992 | Childers |
| 5,258,162 A | 11/1993 | Andersson et al. |
| 5,779,973 A | 7/1998 | Edwards et al. |
| 5,788,925 A | 8/1998 | Pai et al. |
| 5,792,435 A * | 8/1998 | Mueller et al. ............... 422/292 |
| 7,067,089 B2 * | 6/2006 | Wen ........................... 422/292 |
| 7,071,437 B2 * | 7/2006 | Ryan et al. .................. 209/584 |
| 2003/0085147 A1 * | 5/2003 | Gabriele ..................... 206/570 |

FOREIGN PATENT DOCUMENTS

| | | |
|---|---|---|
| GB | 397 057 A | 8/1933 |
| WO | WO 99/32162 A | 7/1999 |
| WO | WO 03/035118 A2 | 5/2003 |

OTHER PUBLICATIONS

English Translation of DE Publication No. 19537630; Adamski, Wolfgang Dipl Ing, Appts. and method for disinfecting sorting plant, Apr. 1997.*

* cited by examiner

DECONTAMINATION SYSTEM FOR MAIL AND OTHER ARTICLES

This application claims the benefit, as a Continuation-In-Part application of U.S. patent application Ser. No. 10/280,950, filed Oct. 25, 2002, now U.S. Pat. No. 7,265,253 and claims the benefit of U.S. Provisional Application Ser. No. 60/401,715, filed Aug. 7, 2002, U.S. Provisional Application Ser. No. 60/416,917, filed Oct. 8, 2002, and U.S. Provisional Application Ser. No. 60/427,191, filed Nov. 18, 2002, the disclosures of which are incorporated herein in their entireties by reference.

BACKGROUND OF THE INVENTION

The present invention relates to decontamination of delivered items to be sorted, such as mail, where there exists a possibility that biological or chemical contaminants may be introduced along with the items to be sorted. It finds particular application in combination with a two-part decontamination system in which the bulk of the items are subjected to a systematic ethylene oxide decontamination process, while the mail determined to be unsuited to ethylene oxide sterilization are treated with a hydrogen peroxide vapor.

Mail sorting facilities, at corporations that are potential terrorist threats or which handle large volumes of mail, face the concern that a letter or package containing a hazardous material, such as a pathogenic bacteria or chemical agent, could enter the facility along with the regular mail. It has been found that mail sorting equipment is capable of releasing spores of *Bacillus anthracis*, the causative agent of anthrax, contained in sealed envelopes into the environment. Simply handling the mail, as in a human sorting operation, also often leads to the release of spores. The airborne spores contaminate other mail and also the sorting equipment, posing hazards both to workers in the sorting room and to mail recipients.

The spores tend to travel beyond the original mail sorting room into other parts of the facility, such as through air ducts, doors, and windows, risking contamination to large areas of the facility. A single contaminated letter is capable of infecting an entire facility. This results in a considerable loss in time while remediation is effected, in addition to the risks posed to workers in the facility.

Workers who sort and examine the mail also tend to contaminate clean areas of the facility when moving between "dirty" and "clean" areas.

The present invention provides a new and improved system and method of treatment of mail which overcome the above-referenced problems and others.

SUMMARY OF THE INVENTION

In accordance with one aspect of the present invention, a method for handling items potentially contaminated with a pathogenic agent is provided. The method includes sorting the potentially contaminated items in an enclosure. At least a portion of the sorted items is treated with a first decontaminant capable of destroying the pathogenic agent. The enclosure is treated with a second decontaminant.

In accordance with another aspect of the present invention, a system for handling items which may be contaminated with a pathogenic agent is provided. The system includes an enclosure for receiving and sorting incoming items. A chamber receives at least a portion of the sorted items from the enclosure and decontaminates the portion of sorted items with a first decontaminant. A source of the first decontaminant is fluidly connected with the chamber. A source of a second decontaminant is fluidly connected with the enclosure for supplying a second decontaminant to the enclosure for decontaminating the enclosure.

In accordance with another aspect of the present invention, a system for handling potentially contaminated items is provided. The system includes an isolator which defines an enclosure capable of being isolated from an exterior environment and an access opening for receiving the items into the enclosure. Means are provided for sorting the items in the enclosure. A chamber is capable of being isolated from an exterior environment. An enclosed passageway selectively connects the enclosure with the chamber, such that at least a portion of the items can be transferred to the chamber from the enclosure without exposure to the exterior environment. A source of a first decontaminant is fluidly connected with the chamber for decontaminating the transferred portion of the items. A source of a second decontaminant is fluidly connected with the enclosure for decontaminating the enclosure and items which have not been transferred to the chamber.

One advantage of at least one embodiment of the present invention is that it enables an unknown sample which is potentially contaminated with biological or chemical pathogens to be aseptically transported, evaluated, and treated according to determined or suspected contaminants.

Another advantage of at least one embodiment of the present invention is that it reduces the hazards posed by potentially contaminated mail.

Another advantage of at least one embodiment of the present invention is that it provides an alternative decontamination method for items which are not conveniently treated with ethylene oxide.

Another advantage of at least one embodiment of the present invention is that there is minimal human contact with potentially contaminated materials.

Another advantage of at least one embodiment of the present invention is that cross contamination between dirty and clean areas is minimized.

Another advantage of at least one embodiment of the present invention is that the area of the potentially contaminated, sorting region is minimized, reducing the complexity of a decontamination process used to render the region free of chemical and biological hazards.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
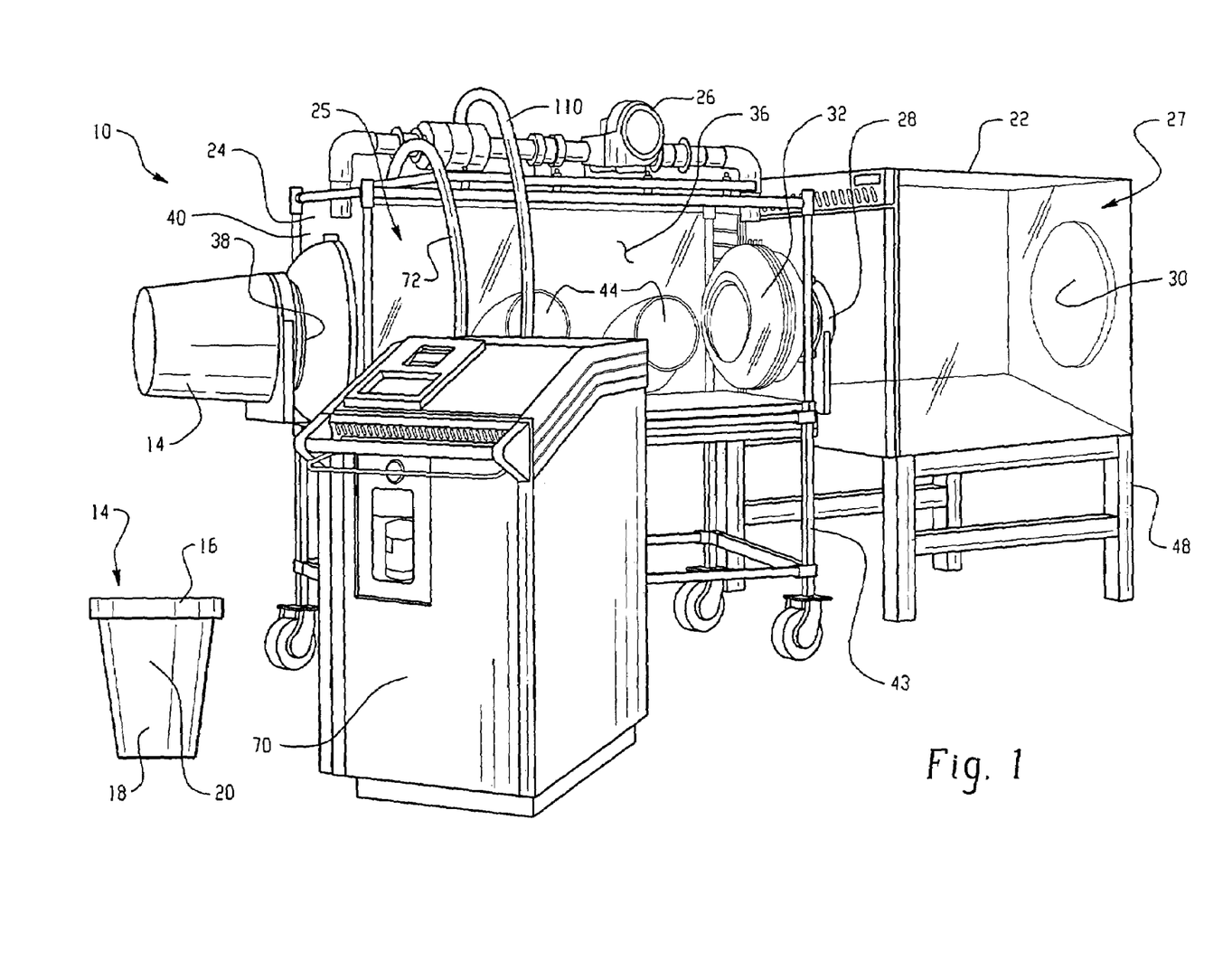
FIG. 1 is a perspective view of a mail handling system in accordance with the present invention.
Figure 2:
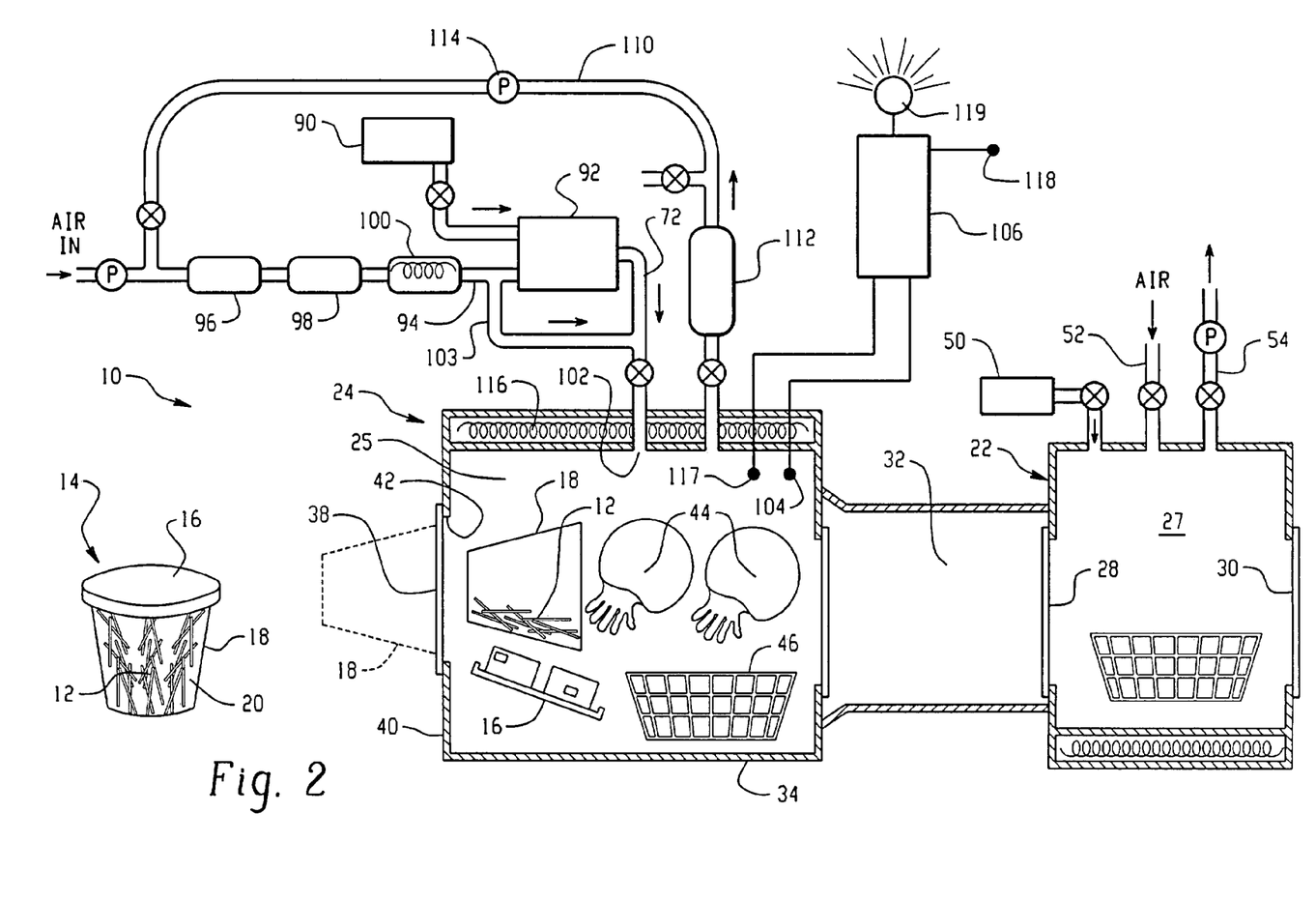
FIG. 2 is a schematic view of the mail handling system of FIG. 1.

With reference to FIGS. 1 and 2, a system 10 for handling items 12, such as mail is shown. The mail handling system is shown as a portable system, allowing it to be moved from room to room or from one facility to another. Exemplary items 12 to be sorted include packages, letters, other items of mail, and/or other potentially suspect items.

The items may enter the facility in containers 14, such as portable totes, each having a lid 16 and a base 18 to provide an enclosed airtight space 20 for the mail when the lid is closed. The totes 14 preferably have their exterior surfaces sprayed with a sporicidal agent, such as SPOR-KLENZ™, available from STERIS Corp., Mentor, Ohio, prior to entering the facility. Optionally, the contents of the totes are examined by a conveyor-type x-ray machine, similar to those used in airports, other type of x-ray scanner, biological or chemical detectors, or combinations thereof for providing an initial evaluation of the contents.

While the system 10 is described with particular reference to handling mail, such as letters and packages, the system is also suited to handling other items, such as products, samples, evidence, equipment, and indeed anything which is capable of being placed within the system.

All incoming mail items are treated as being potentially contaminated with a biological or chemical pathogenic agent (hereinafter both will be referred to simply as pathogenic agents).

The mail handling system 10 includes a pass-through decontamination system 22, designed to destroy any potential pathogenic agents which may be associated with the items. The term "decontamination" and its equivalents is intended to encompass both biological decontamination (including sterilization, disinfection and lesser forms of microbial decontamination, such as sanitization) and well as the destruction of chemical pathogenic agents, or their conversion to harmless compounds.

The system 10 also includes an isolator 24, which defines a sorting enclosure 25 where the mail is examined and items unsuited to the decontamination system are separated from the mail to be treated by the pass through decontamination system 22. The enclosure 25 is preferably about 2m×1m×1.5m in interior volume, although smaller or larger enclosures are also contemplated. The enclosure is capable of being isolated from the surrounding environment during the sorting procedure. For example, the enclosure 25 is completely airtight, or is operated under a negative pressure, such that biological and chemical pathogenic agents present in the mail are not released to the surrounding environment. The enclosure is fluidly connected with a pump 26 or similar device for creating a negative pressure in the enclosure. The enclosure is operated under negative pressure during mail screening/handling, so that any leakage into the isolator is from the "outside to the inside" and thus contamination does not leak outside the enclosure.

Biological pathogenic agents, as used herein means microorganisms, such as bacterial spores, vegetative bacteria, viruses, molds, fungi capable of killing or causing severe injury to mammals, particularly humans. Included among these are viruses, such as equine encephalomyelitis and smallpox; bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Chemical pathogenic agents include poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation. Exemplary chemical pathogenic agents include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl) arsine (commonly known as Lewisite); nerve agents, such as ethyl-N, N dimethyl phosphoramino cyanidate (commonly known as Tabun or agent GA), o-ethyl-S-(2-diisopropyl aminoethyl) methyl phosphono-thiolate (commonly known as agent VX), isopropyl methyl phosphonofluoridate (commonly known as Sarin or Agent GB), methylphosphonofluoridic acid 1,2,2-trimethylpropyl ester (commonly known as Soman or Agent GD).

The term "chemical pathogenic agent" includes substantially pure chemical compounds, but the term also contemplates mixtures of agents in any proportions, as well as those agents in impure states. "Chemical pathogenic agents," as used herein, also includes partially or completely degraded chemical pathogenic agents, e.g., gelled, polymerized, or otherwise partially or totally decomposed chemical warfare agents.

The decontamination system 22 is designed to handle a regular throughput of incoming mail, such as is received daily in a mail sorting facility for a large organization, company, or government body. The decontamination system may be designed to handle all mail entering the facility, or mail may be sorted into classes, and only certain classes of mail subjected to decontamination. Alternatively, different decontamination systems are employed for different classes of mail. For example, remittance mail may be treated with electron beam radiation (e-beam), while other mail is decontaminated with ethylene oxide.

Ethylene oxide is a particularly preferred oxidant for regular treatment of incoming mail and is effective for destruction of commonly known chemical and biological pathogenic agents. It has good materials compatibility, being safe for use with paper, CDs, electronic storage media, video disks, and the like. A preferred decontamination system 22 includes an ethylene oxide sterilizer with a sterilization chamber 27. Although referred to as a "sterilization" chamber, it will be appreciated that chamber 27 is used to destroy both chemical and biological pathogens. Interlocking doors 28, are provided on the "dirty" and "clean" sides of the chamber 27, the dirty side door 28 remaining locked when the clean side door 30 is opened, and vice versa. The entrance door 28, on the dirty side, is connected with the sorting enclosure 25 by an interconnecting passage 32, such as a tunnel or air lock through which potentially contaminated items are loaded into the sterilization chamber 26 without exposure to the surrounding environment. Preferably, the tunnel aseptically interconnects the enclosure 25 and chamber 27. Aseptic connection, here and elsewhere in the application, is preferably accomplished with a triple lip seal approach of the type which is well known in the pharmaceutical industry.

After undergoing a decontamination process, decontaminated items are removed from the chamber 27 through exit door 30 for further sorting and distribution. While ethylene oxide is a particularly preferred decontaminant for mail, other decontamination systems 22 are also contemplated, such as electron beam, gamma radiation, hydrogen peroxide vapor, ultraviolet radiation (UV), or steam decontamination systems.

The isolator 24 includes a housing 34, which defines the enclosure 25. The housing 34 is preferably rigid sided, to withstand pressure changes of slightly above or below atmospheric. The housing is preferably formed, at least in part, from a transparent material, such as plastic or glass. For example, as shown in FIG. 1, a front wall 36 of the housing 34 is formed from a transparent material, or has a window formed therein, with other parts of the housing being formed from metal, such as stainless steel. An aseptic transfer port 38, such as an interlock or door in a side wall 40 of the housing 34 provides access to the enclosure 25 via an access opening 42. In one embodiment, illustrated in FIG. 2, the access opening 42 is sized to receive a tote 14 therethrough, such that the tote can be enclosed within the enclosure 25 when the door 38 is closed. In another embodiment, a portion of the tote base 18, such as a rim of the tote base is configured to engage and interlock with the opening to create an airtight seal between the tote and the opening, as illustrated in FIG. 1. In such cases, the door may be eliminated as the tote base 18 serves as a door.

As shown in FIG. 1, the housing 34 is preferably mounted on a wheeled cart 43, which allows the isolator 24 to be moved to other locations, as needed. Once the tote 14 has been introduced to or connected with the enclosure 25, an operator uses manipulators 44, such as glove box-type gloves, to manipulate the tote 14 and remove the lid 16. The manipulators may alternatively or additionally include a half-body suit. The operator is able to move items inside the isolator without having any direct human exposure. Gloves or half-body suits are made of the appropriate biological or chemically protective material to protect the operators against the anticipated hazardous materials.

Using the gloves 44, the operator removes the mail 12 from the tote and examines it to determine whether the mail contains items which should be excluded from the ethylene oxide sterilizer. Items which may be excluded include foodstuffs, foil packages, which are not readily penetrated, or items, such as leather, which absorb ethylene oxide and release it at a slow rate, making the aeration time too long for practical purposes. The operator may remove some of the packaging of the mail within the enclosure 25 to review the items in greater detail, particularly if an x-ray analysis has not been carried out or is not conclusive of the contents. Those items which are determined to be unsuited to ethylene oxide sterilization/decontamination are put to one side. The remaining mail is loaded by the operator into a vessel 46, such as a wire or plastic basket, suited to use in the ethylene oxide decontamination system 22.

Once the separation process has been completed, the wire basket 46, together with the mail to be ethylene oxide decontaminated, is pushed by the operator, or otherwise conveyed, along the tunnel 32 to the chamber 27 of the ethylene oxide decontamination system 22 and the door 28 closed.

The enclosure 25, its contents, and optionally any remaining mail are preferably subjected to a microbial and/or chemical pathogen decontamination treatment prior to opening the door 38 (FIG. 2) or removing the tote (FIG. 1). Preferably, the decontaminant used in enclosure 25 is one which is capable of destroying both chemical and biological pathogens. In one embodiment, a microbial decontaminant, such as a multicomponent vapor, e.g., hydrogen peroxide, peracetic acid, or combination thereof, is fed into the enclosure 25 for this secondary decontamination treatment. Hydrogen peroxide shows a good activity against a wide range of chemical and biological pathogens.

Although it is anticipated that the decontaminant used in the chamber 27 is different from that used in the enclosure 25, it is also contemplated that alternatively, the same decontaminant is used in both the chamber and the enclosure. For example, different concentrations of the same decontaminant and/or different process conditions may be used (e.g., differences in temperature of decontamination, pressure, exposure time, or the like), depending on the items to be decontaminated.

The ethylene oxide decontamination system 22 may be analogous to those found in hospitals for treating contaminated medical instruments, as described, for example, in U.S. Pat. No. 4,241,010. One such suitable sterilizer is an Eagle 3017 sterilizer obtainable from STERIS Corp. having interlocking double doors and a chamber size of about 5 cu. ft. Such a sterilizer is capable of handling about 2,000-5,000 pieces of mail a day. If larger quantities of mail are to be handled, is preferable to use a number of small sterilizers (i.e., less than about 0.3 $m^3$ chamber size), rather than a larger sterilizer, since the hazards posed by the quantities of ethylene oxide in much larger chambers generally demand the use of blended gas at higher pressures. The decontamination system 22 is optionally supported on the same cart 43 as the housing 34, although it is also contemplated that a separate cart or support surface 48 be used for the sterilizer 22, as shown in FIG. 1.

Prior to ethylene oxide decontamination, the chamber 27 is evacuated to a pressure of about 60-90 torr, or less. Several vacuum pulses are preferably employed to improve removal of air trapped in the items. Ethylene oxide from a cartridge or bulk supply 50 (FIG. 2) is then fed to the chamber 27 to bring the chamber to an above-atmospheric pressure, such as about 0.5-0.6 $kg/cm^2$. During the decontamination phase, the chamber is preferably warmed, for example to about 55° C. The time taken for decontamination depends on the several factors, such as the volume and density of mail items, and the level of assurance desired. For high levels of assurance, e.g., about $10^{-8}$ (no more than 1 in $10^8$ pathogenic species remaining after decontamination), a decontamination time of about 1-4 hours is preferred, most preferably, about 2 hrs.

The chamber 27 is then evacuated and/or aerated to remove residual ethylene oxide from the chamber and items being decontaminated. Ethylene oxide diffuses slowly from "hard" polymers, such as acrylic and amide polymers, polyvinylchloride, and from kraft paper and glassine paper. Thus, a combination of vacuum and aeration is preferably used to speed removal of the residual ethylene oxide. For some items, such as those made from leather, diffusion is so slow that it is preferable to avoid ethylene oxide treatment of these items. One or more aeration cycles may be used in which air is admitted to the chamber through an air inlet line 52 and then removed by vacuum, through an outlet line 54, to ensure that ethylene oxide which has absorbed into the items is removed. Typically, the aeration/evacuation portion of the cycle is longer than the decontamination portion, to ensure that ethylene oxide concentration in the mail is below an acceptably safe level. For example, the aeration portion of the cycle may be about 5-20 hrs, preferably about 10-15 hours. The total time between loading the items through the dirty side door 28 and unloading the decontaminated items via the clean side door 30 is thus about 15 hours.

Optionally, a separate aerator (not shown) is used for final aeration of the processed items, leaving the chamber 27 free to handle another batch of unprocessed mail.

The decontamination of the enclosure 25 is preferably carried out with a gaseous oxidizing agent which serves as a microbial decontaminant and also as a chemical decontaminant, such as hydrogen peroxide in vapor form. Hydrogen peroxide vapor has been shown to be effective against a variety of known biological and chemical pathogenic agents, such as hard to destroy spores of *Bacillus stearothermophilus, Bacillus anthracis*, smallpox virus, and the like. It is also effective at or close to room temperature (e.g., 15-30° C.), making it suitable for decontamination of enclosures with little or no heating. Hydrogen peroxide vapor has a good material compatibility, rendering it safe for use with a variety of equipment and materials, including electronic equipment, such as computers. It also degrades to water and oxygen over time.

To destroy harmful biological pathogens in air and on surfaces throughout the enclosure 25, it has been found that a concentration of hydrogen peroxide of about 1-2 mg/L, or more at about 25° C. is effective to decontaminate the enclosure in about 30 minutes or less. Longer times may be used at lower concentrations or large enclosures, or shorter times at higher concentrations. The vapor is preferably in the "dry" state, i.e., below the saturation point of the vapor, which varies with temperature. This avoids droplets of the vapor condensing on items in the room, which both reduces the effectiveness of the vapor and increases the time needed to remove the residual hydrogen peroxide after the vapor decontamination cycle is complete. Keeping the vapor in the dry state also reduces the risk of damage to electronic components and other items susceptible to water damage.

A source 70 of a decontaminant gas, such as a hydrogen peroxide generation system (FIG. 1) is used to supply the vapor to the enclosure 25, through dedicated ductwork 72. A suitable hydrogen peroxide generation system 70 is a VHP® 1000, available from STERIS Corp, Mentor, Ohio. Such systems are capable of sterilizing enclosures 25 of up to 200,000 cu. ft. For larger enclosures, multiple hydrogen peroxide vapor generators are used. The vapor generation system 70 is preferably small enough that it is portable, and is optionally fitted with wheels (not shown), or the like. Alternatively, the vapor generation system 70 is integral with the isolator.

With particular reference to FIG. 2, the hydrogen peroxide vapor is readily formed from a solution of hydrogen peroxide in water, such as a 35% hydrogen peroxide solution, which is supplied from a reservoir 90, such as a tank, to a vapor generator 92. The generator 92 converts the liquid to a vapor, for example, by bringing droplets or a mist of the solution into contact with a heated plate or tube (not shown). The hydrogen peroxide vapor is delivered via duct 72 to the enclosure 25.

While particular reference is made to hydrogen peroxide, other gaseous oxidizing agents may be used to decontaminate the enclosure, such as peracids, e.g., peracetic acid vapor, ozone, or chlorine gas, alone, or in combination with one or more gaseous oxidants including hydrogen peroxide vapor.

A carrier gas, such as air, is optionally supplied to the vaporizer 92 via a carrier gas line 94 to mix with the liquid and/or vapor and carry the vapor out of the vaporizer 92. The carrier gas may be filtered by a filter 96, dehumidified by a dehumidifier 98, and optionally heated by a heater 100 before entering the vaporizer 92. The vapor and carrier gas mixture is fed into the duct 72 and carried along with the filtered air to an enclosure inlet 102. Alternatively or additionally, a portion of the carrier gas bypasses the vaporizer via a duct 103.

One, or preferably several hydrogen peroxide sensors 104 in the enclosure 25 detect the level of hydrogen peroxide and/or water vapor in the enclosure to ensure that the hydrogen peroxide level in the enclosure is maintained at a preselected level. The sensor 104 is connected with a control system 106, which adjusts the rate of introduction of hydrogen peroxide to the vaporizer, air flow rates, or the like, in response to detected hydrogen peroxide/water concentrations, to maintain the selected hydrogen peroxide concentration in the enclosure 25. Suitable hydrogen peroxide sensors 104 are those which use infrared absorption by the vapor circulating in the enclosure 25. The sensor preferably operates in a region of the infrared spectrum where water and/or hydrogen peroxide absorbs strongly, to provide a measure of the hydrogen peroxide concentration.

In one embodiment, a recirculating system is employed. In this embodiment, the spent vapor is returned to the vaporizer via a return line 110. The spent vapor optionally passes through a catalytic converter 112 to convert residual hydrogen peroxide to water vapor and oxygen prior to reaching the vaporizer 92. As shown in FIG. 2, the returning vapor optionally is passed through the dehumidifier 98 and heater 100 in air inlet line 94 before reentering the vaporizer. The return line is also employed for lowering the humidity of the enclosure prior to admitting hydrogen peroxide. A pump 114 in the return line 110, or elsewhere in the system, draws humid air from the enclosure 25 and passes it through the dehumidifier 98 to reduce the humidity. This reduces the likelihood of condensation of vapor on walls and on mail, which tends to reduce the effectiveness of the vapor decontaminant. Optionally, one or more walls of the housing 34 are heated by a heating element 116, to minimize condensation in the enclosure.

In another embodiment (non-recirculating), spent vapor from the enclosure 25 passes out of the enclosure and is released to atmosphere after passing through the catalytic converter 112.

After the enclosure decontamination phase is complete, the sensors 104 can be used to determine when the levels of hydrogen peroxide in the enclosure 25 have dropped to a level at which it is safe for the operator to reopen the door 38/disengage the tote 14. The operator removes the tote 14 and decontaminated mail from the enclosure 25. The decontaminated mail is disposed of or otherwise dealt with.

The decontamination of the residual mail (if any) and tote 14 in the enclosure 25 may take place contemporaneously with the ethylene oxide decontamination in the chamber 27, or it may take place before or after ethylene oxide decontamination. For effective use of time, the sorting of mail in the enclosure 25 optionally takes place toward the end of the aeration step (i.e., with door 28 closed). In this way, the next batch of mail to be decontaminated can be transported to the sterilizer chamber 27 once the prior batch of decontaminated mail has been removed through door 30, and door 30 closed.

Optionally, the mail handling equipment is located in a room which can be isolated from the rest of a facility in which it is housed and has an independent HVAC system (not shown) for aerating the room. In the event of accidental contamination of the room, the hydrogen peroxide generation system 70 is optionally used to decontaminate the room. Ethylene oxide sensors are preferably located in the room, providing an alarm to workers in the event of a release of the ethylene oxide from the decontamination system.

In one embodiment, automated spray systems are operated from outside the isolatable room to direct a spray or fog over suspected contaminated items. For example, the spray systems may release a liquid spray, fog or mist of an antimicrobial, antiviral, and sporicidal chemical known to be effective against a broad spectrum of known pathogenic agents. One suitable chemical for use as a spray is a liquid mixture of hydrogen peroxide and peracetic acid, which is effective at destroying biological pathogens on surfaces it contacts. Such a composition exhibiting broad spectrum activity is available from STERIS Corp. under the trade name SPOR-KLENZ. This liquid composition is capable of decontaminating a room containing contaminated mail in about fifteen to twenty minutes. It is safe for use with a variety of surfaces, including stainless steel, plastics, glass, floors, and walls.

Within the enclosure 25 and/or surrounding room, detectors 117, 118 optionally detect the presence and/or type of pathogenic agents. Preferably several detectors are provided which detect for different agents. Additionally, several sets of the detectors may be positioned at different locations within the room. U.S. Pat. No. 6,391,624, for example, describes a detector capable of detecting anthrax and other clostridium and bacillus bacteria which may be used for detectors 117, 118. Sensors which incorporate gas chromatography are suited to the detection and/or identification of many chemical pathogens.

The detectors 117, 118 are hooked up to a central control system, such as control system 106, or a separate control system, which signals an alarm 119, such as a flashing light and/or audible alarm, in the event that one or more detectors detects a pathogenic agent at a level above a predetermined threshold level. It is to be appreciated that many pathogenic organisms and chemicals are not readily detected by currently available sensors. Accordingly, the control system 106 has a manual component which relies on worker input in the event that a suspected release of a pathogenic agent has occurred. For example, workers may detect a smell, observe the release of a fine powder from a package, feel nauseous, or suffer other symptoms which they have been trained to associate with the potential release of a pathogenic agent. The alarm may be actuated by a worker who determines that there is a risk of exposure to a suspected pathogenic agent.

Optionally, the type of decontamination process used in the decontamination system and/or in the enclosure is tailored according to the type and/or level of pathogenic agent uncovered. For example, if no pathogenic agents are detected by the detectors, a precautionary decontamination is carried out in the decontamination system, which need not be as rigorous as where a pathogenic agent is actually detected. Or, if certain pathogenic agents are detected which are know to require a more rigorous or particular type of decontamination to ensure destruction, this can be taken into account when selecting the processing conditions. For example, the type of decontaminant(s), length of the decontamination process, concentration of decontaminant, temperature, pressure and/or other factors which affect decontamination are, varied, depending on the type of pathogenic agent detected and/or its concentration.

Figure 3:
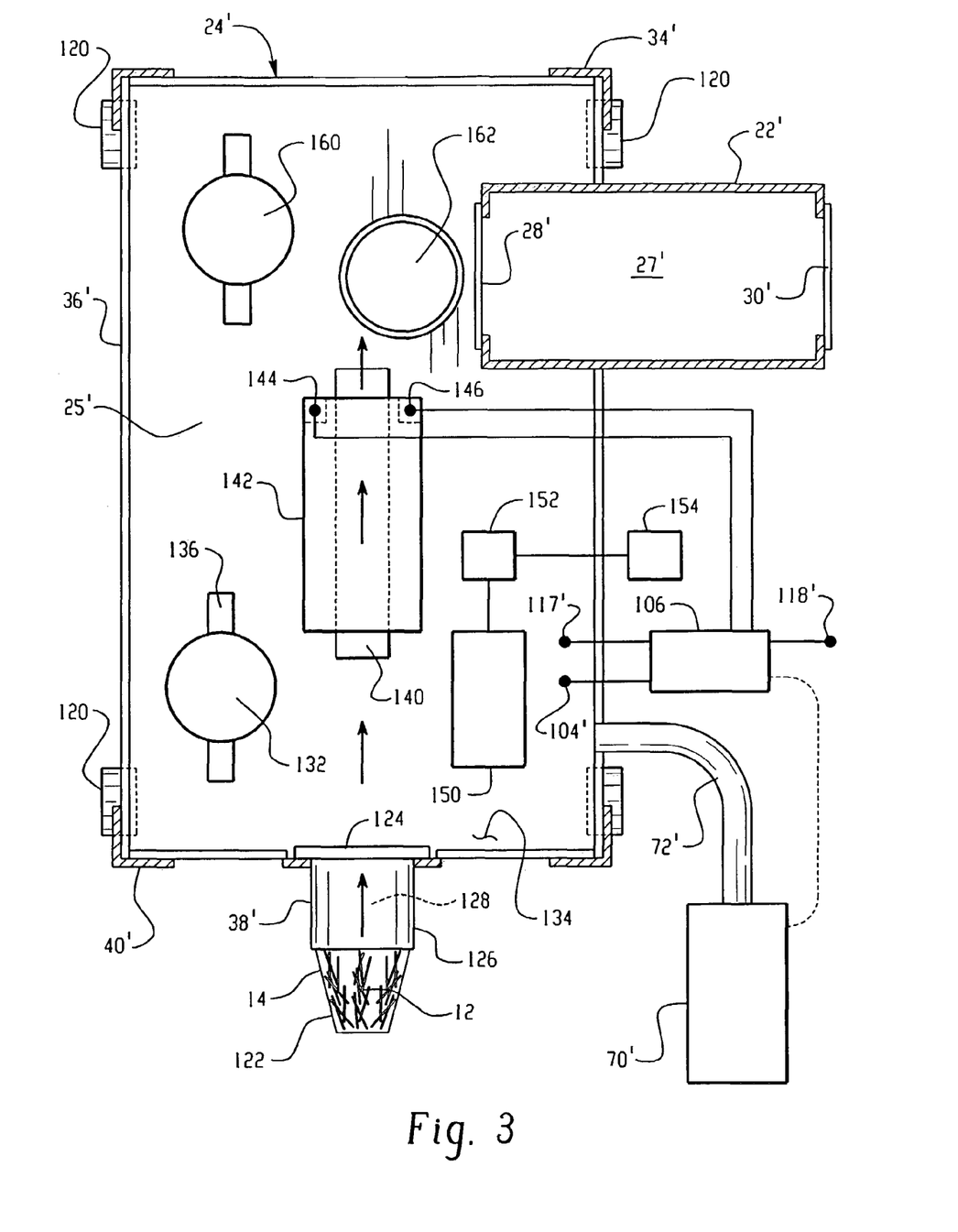
FIG. 3 is a top plan view of an alternative embodiment of an isolator for the mail handling system of FIG. 1.
Figure 4:
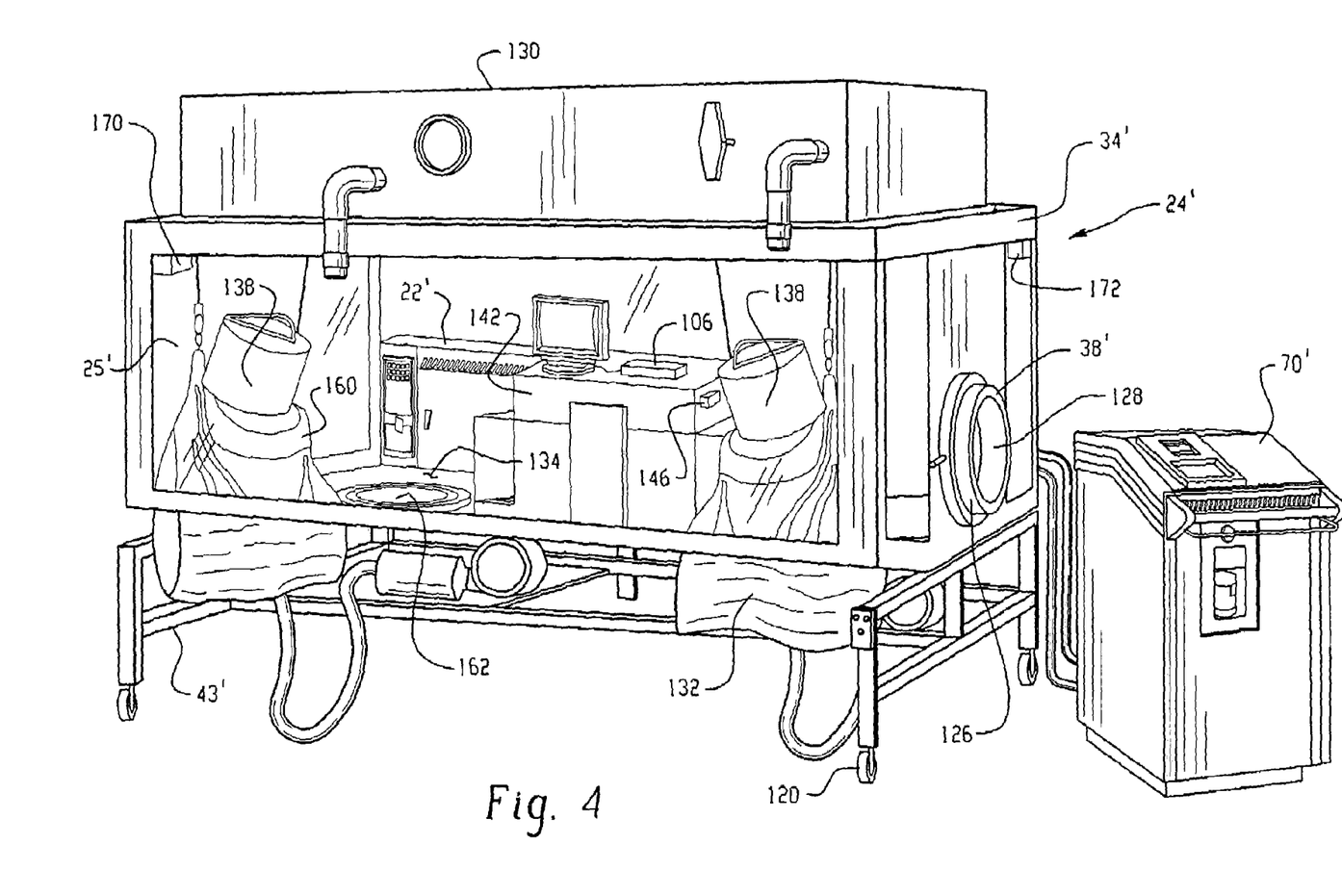
FIG. 4 is a perspective view of the isolator of FIG. 3.

With reference now to FIGS. 3 and 4, where similar elements are numbered with a prime (') and new elements are given new numbers, an isolator 24' is shown. The isolator is similar to isolator 24, except as noted. The isolator includes a housing 34', which defines an enclosure 25'. As for the isolator 24, isolator 24' is optionally transferable from one part of a facility to another. Rollers 120, such as wheels, castors, or other transport mechanisms are mounted to a cart 43' on which the housing is mounted (FIG. 4).

A transfer apparatus 14, such as a tote, is used to transfer the potentially contaminated items 12. Items such as mail, parcels, artifacts, products, or the like that are considered to be potentially contaminated with chemical or biological agents, are loaded into the tote. After closing the tote 14, exterior surfaces 122 of the tote are preferably microbially decontaminated, for example, by spraying with a sporicidal agent, such as SPOR-KLENZ™. The thus treated tote is then carried from a loading area or room to a decontamination area or room, where the isolator 24 and an integral decontamination system 22' are located. Preferably, the loading area is separate from the decontamination room.

In the decontamination room, the items are loaded into the enclosure 25' of the isolator 24' through an aseptic transfer port 38'. The port shown in FIG. 3 has an inner transfer door 124, adjacent the enclosure 25'. With the door 124 closed, the tote is aseptically attached to an exterior portion 126 of the transfer port, which defines a receiving region 128. A negative pressure air system 130 maintains a negative air pressure (slightly below atmospheric pressure) within the enclosure 25' to avoid leakage of potentially contaminated air through any regions which are not completely airtight. The enclosure is operated under negative pressure during mail screening/handling, so that any leakage into the isolator is from the "outside to the inside," therefore contamination does not leak outside the isolator enclosure 25'.

A first half suit 132 is integral with the isolator 24', for example, mounted to a floor 134 of the housing 34', and has manipulating arm and glove portions 136, analogous to manipulators 44. The half suit 132 allows a first operator to position his upper body, including arms and head, operationally in the enclosure 25' while being isolated from the enclosure. A transparent head portion 138 (FIG. 4) permits the operator to view the contents of the enclosure 25'. Alternatively or additionally, manipulators analogous to manipulators 44 shown in FIG. 1 are used.

The first operator opens the transfer door 124 and unloads the contents 12 of the transfer apparatus 14 into the enclosure 25' via the receiving region 128. The operator may visually inspect the items 12. Alternatively, or additionally, the operator loads the items 12 onto a conveyor 140 of an integrated x-ray machine 142, which is located within the enclosure 25'. The x-ray machine is useful for identifying potentially harmful materials, such as ignition sources, e.g., explosive devices or highly flammable materials, such as gasoline. In addition to examination by x-rays, the integrated x-ray machine 142 also includes one or more chemical and/or biological agent detectors 144, 146 which allow the items to be examined for one or more chemical or biological agents. The detectors 144, 146 are preferably linked to a control system 106, which alerts the operator, e.g., via an audible signal or visual display (not shown), in the event that a substance considered to be hazardous is detected. Additionally or alternatively to the x-ray machine 142, equipment capable of detecting explosive or metallic materials is optionally located within the enclosure (e.g., computer tomography (CT) and/or magnetic resonance imaging (MRI) equipment).

A document scanner 150 (FIG. 5) and/or other document reproducing device is optionally located in the enclosure 25'. The document scanner 150 is used to scan documents, or other items removed from all or some of the envelopes or packages 12. The scanned documents are generally those which are required for immediate review (i.e., prior to the completion of the decontamination cycle) or which are considered to be unsuited to the decontamination process. The scanning device 150 creates a scanned image of the document which can then be transmitted electronically outside the enclosure. For example, a processor 152, which may be located within or outside of the enclosure 25', transmits the scanned images to a processor 154 outside the enclosure, such as a personal computer where the scanned images are available for viewing on a screen or are sent to a printer. After scanning, the documents may be destroyed or sent to the decontamination system 22'.

A second operator in a second half suit 160 retrieves the items which have passed through the x-ray machine 142 and evaluates the next step in processing. If the items 12 are considered to be safe, they can be passed through a second, aseptic transfer port 162, which communicates between the isolator enclosure and the outside. FIG. 3 shows the transfer port 160 as being located in the floor 134 of the housing, although other locations are also contemplated. Hazardous materials, which are considered unsuitable for the decontamination system 22, are also passed through the aseptic transfer port 160 for subsequent destruction or other treatment. Preferably, the hazardous items are first bagged or otherwise enclosed in a hazard-proof container. Optionally, the items passed out via port 160 are first subjected to with VHP would to provide a surface decontamination of the items. VHP tends not to penetrate well into paper and other cellulosic materials. The items are then passed out of the isolator aseptically for other alternative decontamination methods (e.g., steam sterilization, hydrogen peroxide vapor for some compatible items, HEPA vacuuming, or the like). Suspect materials, which are considered safe for ethylene oxide, or other suitable decontamination treatment, are loaded directly into a double door decontamination system 22', or optionally introduced via a tunnel, as illustrated in FIG. 1.

It will be appreciated that in place of manipulators 44 and/or half suits 132, 160 used by a human operator, a robot (not shown) within the enclosure 25' is alternatively used to perform some or all of the mail handling tasks under the operation of an operator outside the enclosure. One or more video monitors (not shown) are optionally positioned around the enclosure to allow the operator to view the items being manipulated by the robot.

Other aspects of the isolator 24', including the vapor decontaminant generation system 70', are analogous to the isolator 24 of FIGS. 1-2. As discussed for the embodiment of FIGS. 1-2, a primary purpose of the hydrogen peroxide vapor decontaminant is to decontaminate the interior of the isolator 25, 25' and the equipment inside the isolator in between mail handling so as not to cross contaminate new mail items as they enter the isolator. As with the earlier embodiment, biological and chemical detectors 170, 172 are optionally located inside the isolator 25' and/or surrounding room to detect when chemical or biological contamination is present. If such contaminants are detected, the isolator and its contents may be decontaminated with hydrogen peroxide vapor immediately, or after some of the mail has been transferred to the ethylene oxide decontamination system 22'.

Since the isolator 24, 24' has its own independent air handling system 26, 130 it does not need to be reliant upon the air handling system for the room in which it is located. The isolator can thus be transported from one room or facility to another without requiring changes to the facility. All it requires are conventional power outlets or a generator, and the like. The isolator acts as both the "clean side" and the "dirty side" of a mail handling operation. During mail sorting, the isolator is the dirty side of the system. The hydrogen peroxide vapor system 70, 70', which decontaminates the interior 25, 25' of the isolator and the equipment inside the isolator, enables the conversion of a dirty processing area to a clean processing area. All processing of the mail is preferably conducted inside the isolator so that no facility changes are required. The operators are able to work without the need for full personal protective equipment (PPE) as the half-body suit or gloved handling ports eliminate the need for full PPE with respiratory protection while still offering full protection from exposure to a biological or chemical contaminant.

The embodiments of FIGS. 1-4 are also suited to handling a wide variety of chemical and biological pathogenic agents and items known or suspected of being contaminated therewith. In one embodiment, after the pathogens or contaminated items are loaded into the enclosure, the detectors 117, 117' are used to determine the presence of pathogens and optionally the type of the pathogen present. If a pathogen is detected, the items are transferred to the decontamination system 22 for treatment. The treatment is optionally varied, dependent on the type of pathogen detected. For example, a longer or more rigorous cycle is used where the pathogen detected is known to be particularly hard to destroy. Optionally, the enclosure 25 is not decontaminated if no pathogen is detected. Steam, or other forms of decontamination, could be used in appropriate cases in place of ethylene oxide, such as where steam is an effective decontaminant for the pathogen detected, or for decontamination of liquid items.

In one embodiment, the decontamination system 22 used is selected, based on the nature of the items to be decontaminated, or the type of pathogenic agents detected, or both. For example, the ethylene oxide decontamination system 22 may be disconnected from the airlock 32, wheeled out of the way, and replaced with another decontamination system. For example, if leather goods or battery operated electronic items are identified during the sorting process, a vapor hydrogen peroxide deep vacuum system could replace the ethylene oxide system for treating these items, and optionally other items in the mail which are to be decontaminated. Alternatively, if particular pathogenic agents are sensed by the detectors, this could also be used as a basis for selection of the decontamination system 22, so that the system best suited to destroying the particular pathogenic agent is used.

In another embodiment, two or more airlocks 32 are provided, each one connected to a different decontamination system 22. Optionally, items are categorized, during the sorting process into two (or more) groups, and those best suited to treatment in the first decontamination system transported aseptically there, through the first airlock, while items best suited to treatment in the second decontamination system, transported there aseptically through the second airlock (not shown). Or, one or other of the decontamination systems which is most suited to treatment of all the items/pathogenic agents uncovered is selected for treatment of all the items to be decontaminated in the decontamination system(s). If the items to be decontaminated or the suspected pathogenic agent are known prior to sorting, the most appropriate decontamination system could be selected prior to the sorting stage.

In one embodiment, a system similar to that of FIGS. 1-4 is used but the interlock 38, 38' is formed in a wall of the room in which the isolator 24 is housed. Items to be evaluated and decontaminated are loaded into the enclosure through the interlock, without entering the room. There is thus no need for the items to be placed in a container 12 in this embodiment. Personnel handling the contaminated or suspect items wear hazard protection suits.

The invention has been described with reference to the preferred embodiment. Obviously, modifications and alterations will occur to others upon reading and understanding the preceding detailed description. It is intended that the invention, be construed as including all such modifications and alterations insofar as they come within the scope of the appended claims or the equivalents thereof.

Having thus described the preferred embodiment, the invention is now claimed to be:

1. A method for handling items potentially contaminated with a pathogenic agent comprising:
   sorting the potentially contaminated items in an enclosure to separate items which are unsuited to treatment with a first decontaminant from remaining potentially contaminated items;
   treating at least a portion of the sorted items with the first decontaminant capable of destroying the pathogenic agent; and
   treating the enclosure with a second decontaminant.

2. The method of claim 1, wherein the first decontaminant includes an oxidizing gas.

3. The method of claim 2, wherein the oxidizing gas includes ethylene oxide.

4. The method of claim 1, wherein the second decontaminant includes an antimicrobial vapor.

5. The method of claim 4, wherein the antimicrobial vapor includes hydrogen peroxide.

6. The method of claim 1, further including, prior to the step of sorting:
introducing the items to the enclosure in a sealed container.

7. The method of claim 6, wherein the step of introducing the items to the enclosure in the sealed container includes:
connecting the sealed container containing the items with an interlock which selectively provides access to the enclosure while forming a seal between the container and the interlock;
with the container connected to the interlock, opening the container to the enclosure; and
introducing the items to the enclosure from the container.

8. The method of claim 1, wherein the enclosure is airtight or is operated under a negative pressure.

9. The method of claim 1, wherein the step of sorting includes:
using manipulators to sort the items; and
placing the items to be decontaminated with the first decontaminant in a basket.

10. The method of claim 1, further including:
loading the at least a portion of the items into a basket;
transporting the basket into the chamber of a sterilizer connected with the enclosure;
evacuating the sterilizer chamber; and
introducing gaseous sterilant to the chamber, the items being kept in the sterilizer for a sufficient time to decontaminate the items.

11. The method of claim 10, further including, after the introducing step:
aerating the chamber to remove residual sterilant.

12. The method of claim 1, further including, within the enclosure, examining at least a portion of the items with an x-ray machine.

13. The method of claim 1, wherein the items include mailed items.

14. The method of claim 13, further including:
scanning a document in the mail with a scanning device within the enclosure to generate a scanned image; and
transmitting the scanned image to a location outside the enclosure.

15. The method of claim 1, further including:
employing at least one detector capable of detecting at least one pathogenic agent when present at a detectable level within the enclosure.

16. The method of claim 15, further including:
tailoring at least one of the step of treating the enclosure with a second decontaminant and the step of treating at least a portion of the sorted items with a first decontaminant according to at least one of a type of pathogenic agent detected and a level of the pathogenic agent detected to improve the effectiveness of the at least one step.

17. The method of claim 1, wherein the step of treating the enclosure with the second decontaminant is performed after the items have been removed from the enclosure.

18. The method of claim 1 wherein the sorting step is performed prior to treating the sorted items.

19. A method for handling items potentially contaminated with a pathogenic agent comprising:
sorting the potentially contaminated items in an enclosure;
thereafter, treating at least a portion of the sorted items with a first decontaminant capable of destroying the pathogenic agent in a chamber which is selectively connected with the enclosure and is isolatable from the enclosure; and
treating the enclosure with a second decontaminant.

20. The method of claim 19, further including, prior to the step of treating at least a portion of the items with a first decontaminant:
transporting the at least a portion of the items from the enclosure to the chamber connected with the enclosure; and
closing off the chamber from the enclosure.

21. The method of claim 19, wherein the sorting step sorts items between items which are not suited to treatment by the first decontaminant and items which are suited for treatment by the first decontaminant.

22. A method for handling items potentially contaminated with a pathogenic agent composing:
(a) transporting the items in a sealed container;
(b) connecting the sealed container to an isolated enclosure in an airtight manner:
(c) using manipulators, opening the container to an interior of the enclosure, removing the items from the container into the enclosure, and sorting the items within the isolated enclosure;
(d) opening an outlet door between the isolated enclosure and an isolated region;
(e) moving at least a portion of the sorted items through the outlet door and the isolated region into a sealable decontamination chamber;
(f) sealing the decontamination chamber from the enclosure;
(g) treating the portion of the sorted items in the decontamination chamber with a first decontaminant capable of destroying the pathogenic agent;
(h) treating the enclosure with a second decontaminant; and
(i) while the portion of the sorted items is being treated in the decontamination chamber, receiving and sorting additional items in the isolated enclosure.

23. The method of claim 22, further including:
after treating the portion of the sorted items in the decontamination chamber, removing the treated items directly to atmosphere without going through the enclosure.

24. The method of claim 22, wherein the enclosure is treated with the second decontaminant after the items have been removed.

25. The method of claim 22, wherein treating the portion of the sorted items in the decontamination chamber includes:
evacuating the decontamination chamber;
introducing gaseous ethylene oxide;
removing the ethylene oxide from the decontamination chamber; and
aerating the sorted items in the decontamination chamber to remove absorbed ethylene oxide.

26. The method of claim 25, wherein the second decontaminant used to treat the enclosure includes hydrogen peroxide vapor.

* * * * *